United States Patent
Eisen-Nevo et al.

(10) Patent No.: US 7,473,780 B2
(45) Date of Patent: Jan. 6, 2009

(54) DRYING PROCESS FOR PREPARING CRYSTALLINE SOLID FAMCICLOVIR

(75) Inventors: Hagit Eisen-Nevo, Petah-Tikva (IL); Dalia Maidan-Hanoch, Kfar-Yona (IL)

(73) Assignee: Teva Pharmeceutical Industries Ltd., Petah Tiqva (IL)

( * ) Notice: Subject to any disclaimer, the term of this patent is extended or adjusted under 35 U.S.C. 154(b) by 427 days.

(21) Appl. No.: 11/131,119

(22) Filed: May 18, 2005

(65) Prior Publication Data

US 2006/0004027 A1    Jan. 5, 2006

Related U.S. Application Data

(60) Provisional application No. 60/572,526, filed on May 18, 2004.

(51) Int. Cl.
C07D 473/32 (2006.01)
(52) U.S. Cl. .................................................. 544/277
(58) Field of Classification Search ................ 544/277
See application file for complete search history.

(56) References Cited

U.S. PATENT DOCUMENTS

| | | | |
|---|---|---|---|
| 5,017,701 A * | 5/1991 | Grinter et al. | 544/276 |
| 5,066,805 A * | 11/1991 | Kincey | 544/277 |
| 5,138,057 A * | 8/1992 | Geen et al. | 544/277 |
| 5,246,937 A * | 9/1993 | Harnden et al. | 514/263.4 |
| 6,342,603 B1* | 1/2002 | Hayashi et al. | 544/264 |
| 6,437,125 B1* | 8/2002 | Geen et al. | 544/276 |
| 6,846,927 B1* | 1/2005 | Dales | 544/276 |
| 2003/0134864 A1* | 7/2003 | Campbell et al. | 514/263.4 |
| 2004/0097528 A1* | 5/2004 | Dolitzky et al. | 514/263.4 |
| 2008/0154038 A1* | 6/2008 | Chiodini et al. | 544/277 |

FOREIGN PATENT DOCUMENTS

| | | |
|---|---|---|
| WO | WO 95/28402 | 10/1995 |
| WO | WO 97/29108 | 8/1997 |
| WO | WO 00/06573 A1 * | 2/2000 |
| WO | WO 2004/018470 | 3/2004 |
| WO | WO 2004/099208 | 11/2004 |

OTHER PUBLICATIONS

Harnden, Richard L. Jarvest, Malcolm R. Boyd, David Sutton, and R. Anthony Vere Hodge J. Med. Chem. 1989; 32(8) 1738-1743.*
Briony Brand, et al., Tetrahedron, vol. 55, Issue 16, Apr. 16, 1999, pp. 5239-5252.*
Richard Freer et al., Tetrahedron, vol. 56, Issue 26, Jun. 23, 2000, pp. 4589-4595.*
Wang, et al., Jilin Daxue Ziran Kexue Xuebao (2000), (1), 95-98.*
Translation of Wang, et al., Jilin Daxue Ziran Kexue Xuebao (2000), (1), 95-98.*
Geen et al., Tetrahedron letters 33, 4609 (1992).*
"Nucleosides & Nucleotides" 9(4): 499-513 (1990), Harnden et al.
Search Report of ROC (Taiwan) Application No. 094116100, dated Jun. 27, 2007.
International Search Report of Application No. PCT/US2005/017282, dated Aug. 28, 2005.

* cited by examiner

*Primary Examiner*—Mark L Berch
(74) *Attorney, Agent, or Firm*—Kenyon & Kenyon LLP

(57) ABSTRACT

The present invention provides a drying process for preparing crystalline solid famciclovir form I comprising the steps of: i) preparing a wet crystalline form of famciclovir; ii) drying the wet crystalline form of famciclovir at a temperature of below 50° C. until the crystalline form contains less than 15% (wt/wt) wetness; and iii) drying the wet crystalline form of famciclovir at a temperature of above 50° C. until the wet crystalline form of famciclovir contains less than 0.05% (wt/wt) water to obtain crystalline solid famciclovir form I.

23 Claims, 3 Drawing Sheets

DRYING PROCESS FOR PREPARING CRYSTALLINE SOLID FAMCICLOVIR

CROSS REFERENCE TO RELATED APPLICATION

This application claims the benefit of U.S. Provisional Application No. 60/572,526, filed May 18, 2004, the disclosure of which is incorporated by reference.

FIELD OF THE INVENTION

The present invention relates to a drying process for preparing crystalline solid famciclovir.

BACKGROUND OF THE INVENTION

Famciclovir is an antiviral drug marketed by SmithKline Beecham and is available as Famvir®. Famvir® is indicated for the treatment of acute herpes zoster (shingles). It is also indicated for treatment or suppression of recurrent genital herpes in immunocompetent patients and for treatment of recurrent mucocutaneous herpes simplex infections in HIV infected patients. The chemical name for famciclovir is 2-[2-(2-amino-9H-purin-9-yl)ethyl]-1,3-propane diacetate.

U.S. Pat. No. 5,246,937 discloses purine derivatives including famciclovir as antiviral compounds. WO 97/29108 and EP 0 885 223 B1 describe an anhydrous form and a monohydrate form of famciclovir. These patent publications state that the anhydrous form of famciclovir is prior art; however, there is no physicochemical characterization of either the anhydrous or monohydrate forms. Moreover, there is no disclosure in these patent publications of any experimental data (e.g., XRD, FTIR, and DSC) with respect to these two forms. Crystallographic data for famciclovir monohydrate are given in *Nucleosides & Nucleotides* 9(4): 499-513 (1990).

A particular polymorphic form may also give rise to distinct spectroscopic properties that may be detectable by powder X-ray diffraction, solid state $^{13}C$ NMR spectrometry or infrared spectrometry. Based on the physical characterization, various crystalline solid forms for famciclovir have been described in WO 2004/018470; namely, anhydrous famciclovir denominated as crystalline solid famciclovir forms I, II and III.

Different crystalline solid forms of famciclovir may have different solid state physical properties, thermal stability, cost of preparation, dissolution characteristics and bioavailability. Accordingly, this may affect the flowability of the milled solid and hence affects the ease with which the material is handled during processing. In addition, crystalline solid state of a famciclovir polymorph may affect its rate of dissolution in aqueous fluid (e.g., in a patient's stomach fluid) that can have therapeutic consequences, together with its behavior on compaction and storage stability.

There are two problems regarding the production of famciclovir. First, the drying procedure for famciclovir is difficult. The melting points for the dried famciclovir and crystalline forms of famciclovir are approximately 102° C. When the crystalline solid famciclovir form is wet, its melting point decreases. Second, it is difficult to obtain substantially pure crystalline solid famciclovir form I by convenient crystallization methods. Crystalline solid famciclovir form I is often obtained with a high contamination from other famciclovir forms.

There is a constant need for a developping a better drying process in preparing a good crystalline solid form of famciclovir; in particular, famciclovir form I that can provide a better pharmaceutical composition suitable for use in tablet or capsule due to good stability, handling qualities and like properties.

SUMMARY OF THE INVENTION

In one embodiment, the present invention provides a process for preparing crystalline famciclovir, comprising the steps of:

a) providing a wet crystalline form of famciclovir containing about 40% (wt/wt) or less solvent such as from about 5% to about 40% (wt/wt), preferably about 15% to about 40% (wt/wt), or from about 5% to about 20% (wt/wt), solvent;

b) drying the wet crystalline form of famciclovir of step a) at a temperature of from about 30° C. to about 50° C., and c) further drying the wet crystalline form of famciclovir obtained from step b), wherein the wet crystalline form of famciclovir preferably contains less than about 15% (wt/wt) solvent, at a temperature higher than 50° C. to obtain a crystalline form of famciclovir containing less than about 1% (wt/wt), preferably less than about 0.5% (wt/wt) solvent, more preferably less than about 0.2% (wt/wt), and even more preferably less than about 0.05% (wt/wt) solvent.

In another embodiment, the present invention provides a process for preparing crystalline famciclovir, comprising the steps of:

a) providing a wet crystalline form of famciclovir containing more than about 40% (wt/wt) solvent;

b) drying the wet crystalline form of famciclovir at a temperature of from about 25° C. to about 35° C., to obtain a wet crystalline form of famciclovir containing about 40% (wt/wt) or less solvent;

c) further drying the wet crystalline form of famciclovir at a temperature of from about 30° C. to about 50° C., to obtain a wet crystalline form of famciclovir, preferably containing less than 15% (wt/wt) solvent; and d) further drying the wet crystalline form of famciclovir at a temperature higher than 50° C., to obtain a crystalline form of famciclovir containing less than 1% (wt/wt) solvent, preferably less than about 0.5% (wt/wt) solvent, more preferably less than about 0.2% (wt/wt) solvent, and even more preferably less than about 0.05% (wt/wt) solvent.

When the solvent in the above processes is water, the obtained product is famciclovir Form I.

Preferably, the crystalline form of famciclovir obtained in the above processes, is famciclovir Form I containing less than about 10% (wt/wt) of another crystalline form, especially famciclovir Form II. Most preferably, the Form I obtained by these processes contains less than 2% (wt/wt) of another crystalline form, especially famciclovir Form II.

DETAILED DESCRIPTION OF THE INVENTION

Figure 1:
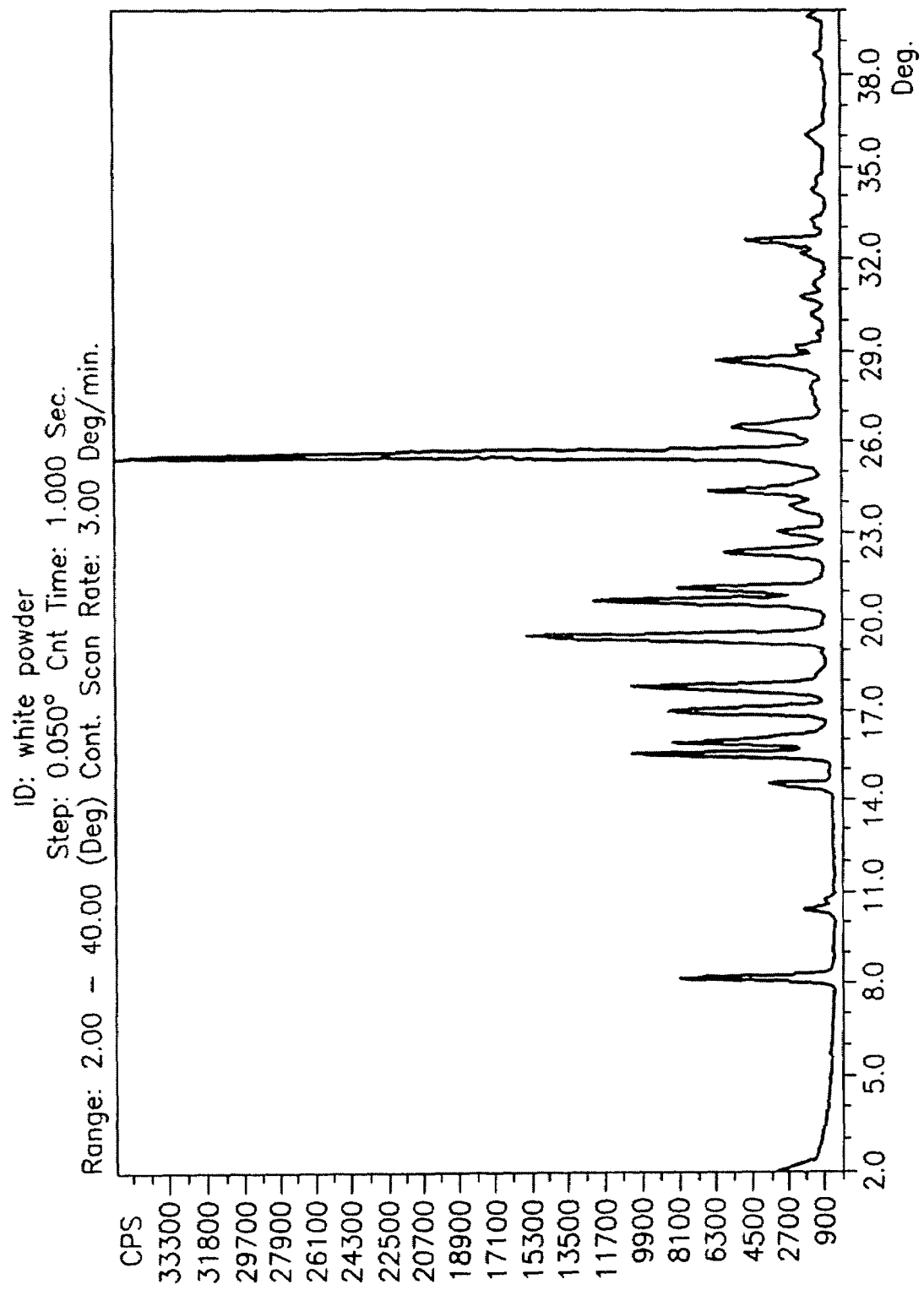
FIG. 1 depicts a XRD diffractogram of crystalline solid famciclovir Form I.

Unless otherwise specified, the term "crystalline form of famciclovir" when used as a starting material to prepare the various crystalline solid forms of famciclovir, refers to a mixture of crystalline solid famciclovir Form I and crystalline solid famciclovir Form II.

For the purpose of avoiding melting the material, it is preferred to dry the famciclovir material to a lower wetness stage at a lower temperature in comparison with the melting point, before moving to the next temperature stage. Therefore, crystalline famciclovir is preferably dried at a temperature ranging from higher than 50° C. to 65° C. until the solvent content is low enough, and then, in order to accelerate the process, the temperature can be elevated to as high as 80° C.

The following table exemplifies the wetness percents in which the material is melting:

| Melting point-Temperature | Wetness (%) (wt/wt) |
| --- | --- |
| 45° C. | 40% |
| 65° C. | 15% |

It is possible to dry, by heating at or below the temperature shown in the above table, the material with wetness at or below the corresponding specific wetness shown in the table. For example, if the starting famciclovir material contains over 20% (wt/wt) of wetness, it is desirable to first heating the material up to a temperature of about 45° C. to obtain wetness of below 15%, and then it is desirable to heat the material to 65° C.

In one embodiment of the process of the present invention, when the starting material contains less than about 40%, preferably about 15-40% (wt/wt) solvent, the process comprises drying the wet crystalline form of famciclovir at a temperature of from about 30° C. to about 50° C., preferably at a temperature of from about 40° C. to about 50° C., more preferably at a temperature of about 45° C., until a wet crystalline form of famciclovir containing less than 15% (wt/wt) solvent is obtained, then further drying at a temperature higher than 50° C., preferably at a temperature ranging from higher than about 50° C. to about 80° C., more preferably at a temperature ranging from higher than about 50° C. to about 65° C., until famciclovir crystalline form containing less than 1% (wt/wt) solvent is obtained. The process further includes drying the crystalline famciclovir containing less than 1% (wt/wt) solvent at a temperature ranging from higher than about 50° C. to about 80° C. to obtain famciclovir crystalline form containing less than about 0.5% (wt/wt) solvent, more preferably less than about 0.2% (wt/wt) solvent, and even more preferably less than about 0.05% (wt/wt) solvent.

Optionally, the starting material containing less than about 40% (wt/wt) solvent is further washed with a solvent prior the drying process described above, to obtain a wet crystalline form of famciclovir containing more than 40% solvent. The obtained wet crystalline form of famciclovir containing more than 40% solvent is then dried at a temperature of from about 25° C. to about 35° C., until obtaining the wet crystalline form of famciclovir that contains 40% (wt/wt) or less solvent.

In another embodiment of the process of the present invention, when the starting material contains more than 40% (wt/wt) solvent, the process comprises drying the wet crystalline form of famciclovir at a temperature of from about 25° C. to about 35° C., until the wet crystalline form of famciclovir contains 40% (wt/wt) or less solvent is obtained. Then the processes further comprises drying the wet crystalline form containing about 40% (wt/wt) or less solvent at a temperature of from about 30° C. to about 50° C., preferably at a temperature of from about 40° C. to about 50° C., more preferably at a temperature of about 45° C., until a wet crystalline form of fmciclovir contains less than 15% (wt/wt) solvent is obtained, then further drying at a temperature higher than 50° C., preferably at a temperature ranging from higher than about 50° C. to about 80° C., more preferably at a temperature ranging from higher than about 50° C. to about 65° C., until a famciclovir crystalline form containing less than 1% (wt/wt) solvent is obtained. The process further includes drying the crystalline famciclovir containing less than 1% (wt/wt) solvent at a temperature ranging from higher than about 50° C. to about 80° C. to obtain a famciclovir crystalline form containing less than 0.5% (wt/wt) solvent, more preferably less than about 0.2% (wt/wt) solvent and even more preferably less than about 0.05% (wt/wt) solvent.

In the processes for preparing crystalline famciclovir of the present invention, the solvent is preferably selected from the group consisting of water, $C_{1-4}$ alcohols, $C_{5-8}$ alkanes, diisopropyl ether, Class 3 solvents and mixtures thereof.

Class 3 solvents are described in the ICH Harmonized Tripartite Guideline, Impurities: Guideline for Residual Solvents. Class 3 solvents are described as less toxic and of lower risk to human health, and include solvents with known human health hazards normally accepted in pharmaceuticals. Class 3 solvents can be selected from the group consisting of: acetic acid, acetone, 1-butanol, 2-butanol, butyl acetate, tert-buthylmethyl ether, dimethyl sulfoxide, ethanol, ethyl acetate, ethyl ether, ethyl formate, formic acid, heptane, isobutyl acetate, isopropyl acetate, methyl acetate, 3-methyl-1-butanol, methylethyl ketone, methylisobutylketone, 2-methyl-1-propanol, pentane, 1-pentanol, 1-propanol, 2-propanol, and propyl acetate.

The above processes may further comprise washing the wet crystalline form of famciclovir before the drying process.

Preferably, the drying in the above processes is performed at a reduced pressure; preferably less than 65 mmHg, and more preferably less than 30 mmHg, and even more preferably a high vacuum such as less than 5 mmHg. The drying is performed under vacuum in a tray oven (Static Drying), a stirred dryer, or fluidized bed. Optionally, fast mixing in a stirred dryer may be used to accelerate the drying process; however, it may result in breaking the crystals.

In yet another embodiment, the invention comprises crystalline form of famciclovir containing less than about 1% (wt/wt) solvent and preferably less than about 0.5% (wt/wt) solvent. More preferably, the crystalline form contains less than about 0.2% (wt/wt) solvent and, even more preferably, less than about 0.05% (wt/wt) solvent. Preferably, the crystalline form is famciclovir Form I.

When the starting material in the above processes, contains water as a solvent, famciclovir Form I is obtained. The famciclovir Form I obtained by these processes contains less than about 10% (wt/wt) of another crystalline form, especially famciclovir Form II. Most preferably, the Form I obtained by these processes contains less than 2% (wt/wt) of another crystalline form, especially famciclovir Form II.

The water content disclosed herein is based on measurements by Karl Fischer.

Crystalline Solid Famciclovir Forms

Figure 2:
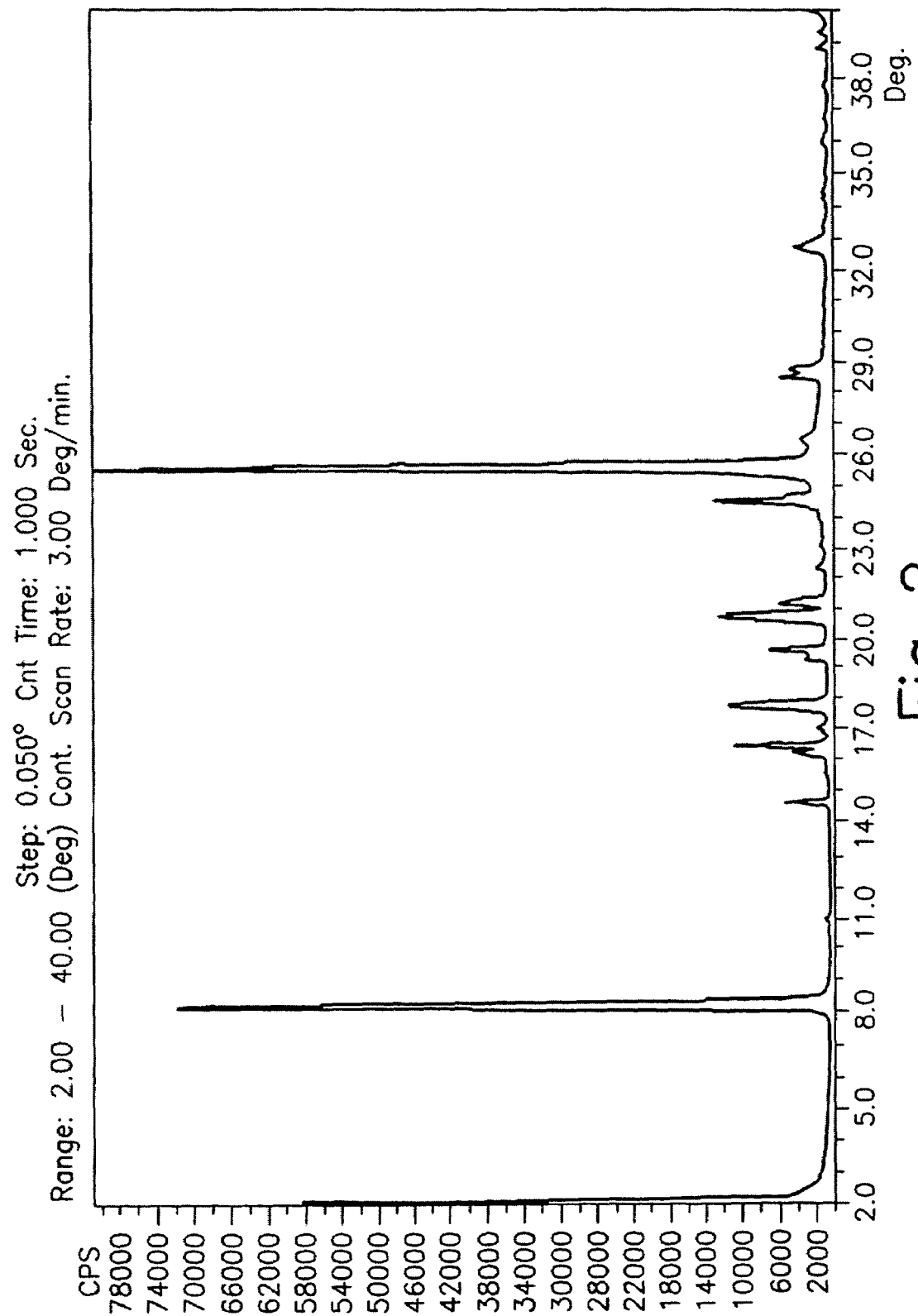
FIG. 2 depicts a XRD diffractogram of crystalline solid famciclovir Form II.
Figure 3:
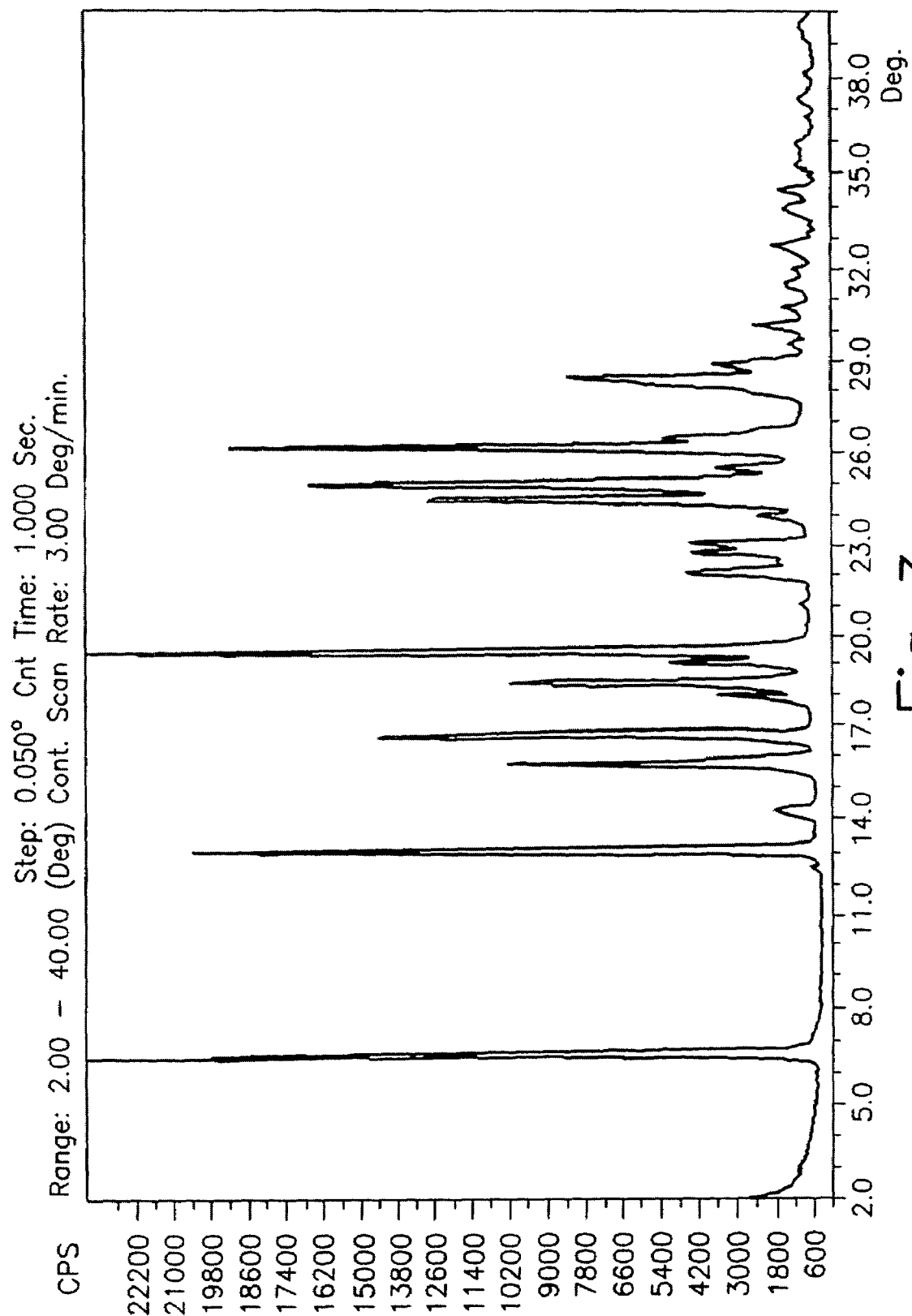
FIG. 3 depicts a XRD diffractogram of crystalline solid famciclovir Form III.

Powder X-ray diffraction patterns for crystalline solid forms of famciclovir were obtained by methods known in the art using a Scintag X'TRA X-ray powder diffractometer, equipped with a solid state Si(Li) detector thermoelectrically cooled, at scanning speed of 3° min.$^{-1}$ scanning range 2-40 degrees two-theta. Copper radiation of λ=1.5418 was used.

i) Crystalline Solid Famciclovir form I:

The obtained crystalline solid famciclovir form I was characterized by XRD peaks at 15.5 and 15.9±0.2 deg. 2θ as shown in FIG. 1. Other XRD peaks observed at 8.2, 10.4, 14.5, 17.0, 17.7, 19.5, 20.6, 21.1, 22.3, 23.0, 23.9, 24.4, 25.6, 26.5, 28.6, 29.0 and 32.6±0.2 deg. 2θ.

ii) Crystalline Solid Famciclovir form II:

The obtained crystalline solid famciclovir form II was characterized by XRD peaks at 16.2 and 16.4±0.2 deg. 2θ as shown in FIG. 2. Other XRD peaks observed at 8.3, 14.6, 17.0, 17.8, 19.3, 19.7, 20.7, 21.2, 24.5, 25.6, 26.5, 28.5 and 32.6±0.2 deg. 2θ.

iii) Crystalline Solid Famciclovir form III:

The obtained crystalline solid famciclovir form III (a methanol solvate) was characterized by the XRD peaks at 6.6 and 13.0±0.2 deg. 2θ as shown in FIG. 3. Other XRD peaks observed at 15.9, 16.7, 17.9, 18.4, 19.1, 19.6, 22.1, 22.8, 23.1, 24.5, 25.0, 26.2, 28.4 and 28.8±0.2 deg. 2θ.

The present invention is further illustrated by the following examples, which describe the preparation of famciclovir and examples in drying famciclovir, without any limiting any scope of the invention. These examples are intended to illustrate the benefits of the present invention, but do not necessarily exemplify the full scope of the invention.

EXAMPLES

Water and solvent content were measured by Mettler (Halogen Moisture Analyzer): Mettler HB43, "Mettler Toledo".

The famciclovir used in the following examples as the starting material can be prepared according to U.S. Pat. No. 5,246,937.

Example 1

Drying in 0.25 Liter Stirred Reactor (30 Grams)

30 grams of wet famciclovir were washed with water. The material was dried in a stirred reactor. Form 1 was obtained. The following table describes the drying process and its conditions.

| Sample no. | Starting material wetness (%) | Drying Temperature (°C.) | Drying time (Hours) | Wetness During the drying process % | Pressure (mmHg) | Stirring rate (Rounds per minute) |
|---|---|---|---|---|---|---|
| X 1 | 11.17 | 45 | 2 | 5.3 | 70 | 12 |
| X 2 |  | 45 | 4 | 3.89 |  |  |
| X 3 |  | 45 | 6 | 1.77 |  |  |
| X 4 |  | 65 | 8.3 | 0 |  |  |
| X 5 |  | 65 | 21 | 0.03 |  |  |

Example 2

Drying in 0.25 Liter (30 Grams)

30 grams of wet famciclovir were washed with water. The material was dried in a stirred reactor. Form 1 was obtained. The following table describes the drying process and its conditions.

| Sample no. | Starting material wetness (%) | Drying Temperature (°C.) | Drying time (Hours) | Wetness During the drying process % | Pressure (mmHg) | Stirring rate (Rounds per minute) |
|---|---|---|---|---|---|---|
| Y 1 | 9.8 | 45 | 2 | 5.23 | 93-96 | 100 |
| Y 2 |  | 45 | 4 | 3.53 | 92 |  |
| Y 3 |  | 45 | 6 | 1.8 | 89 |  |
| Y 4 |  | 65 | 8 | 0.2 | 89 |  |
| Y 5 |  | 65 | 21 | 0.05 | 75 |  |

Example 3

Drying in 0.25 Liter (30 Grams)

30 grams of wet famciclovir were washed with water. The material was dried in a stirred reactor. Form 1 was obtained. The following table describes the drying process and its conditions.

| Sample no. | Starting material wetness (%) | Drying Temperature (°C.) | Drying time (Hours) | Wetness During the drying process % | Pressure (mmHg) | Stirring rate (Rounds per minute) |
|---|---|---|---|---|---|---|
| Z 1 | 15.83 | 30 | 1.05 | 16.35 | 89 | 12 |
| Z 2 |  | 30 | 1.45 | 15.73 | 92 |  |
| Z 3 |  | 30 | 3.05 | 11.52 | 92 |  |
| Z 4 |  | 30 | 4.45 | 9.13 | 60 |  |
| Z 5 |  | 30 | 6.1 | 8.94 | 60 |  |
| Z 6 |  | 45 | 8.5 | 4.59 | 60 |  |
| Z 7 |  | 65 | 9.75 | 1.62 | 60 |  |
| Z 8 |  | 65 | 22 | 0.04 | 60 |  |

Example 4

Drying in 0.25 Liter (30 Grams)

30 grams of wet famciclovir were washed with water. The material was dried in a stirred reactor. Form 1 was obtained. The following table describes the drying process and its conditions.

| Sample no. | Starting material wetness (%) | Drying Temperature (°C.) | Drying time (Hours) | Wetness During the drying process % | Pressure (mmHg) | Stirring rate (Rounds per minute) |
|---|---|---|---|---|---|---|
| H 1 | 12.3 | 30 | 2 | 5.11 | 64 | 80 |
| H 2 |  | 45 | 4 | 1.89 | 70 |  |
| H 3 |  | 80 | 6 | 0 | 59 |  |
| H 4 |  | 80 | 23 | 0.15 | 170 |  |

Example 5

Drying in 0.25 Liter (30 Grams)

30 grams of wet famciclovir were washed with water. The material was dried in a stirred reactor. Form 1 was obtained. The following table describes the drying process and its conditions.

| Sample no. | Starting material wetness (%) | Drying Temperature (° C.) | Drying time (Hours) | Wetness During the drying process % | Pressure (mmHg) | Stirring rate (Rounds per minute) |
|---|---|---|---|---|---|---|
| G 1 | 12.3 | 30 | 2.05 | 6.42 | 75 | Without mixing |
| G 2 | | 45 | 4.15 | 5.25 | 68 | 12 |
| G 3 | | 80 | 6.15 | 2.32 | 68 | |
| G 4 | | 80 | 8.15 | 0.59 | 72 | |
| G 5 | | 80 | 23 | 0 | 58 | |

Example 6

Drying in 200 Grams Scale 200 grams of wet famciclovir were washed with water. The material was dried in a stirred reactor. Form 1 was obtained. The following table describes the drying process and its conditions.

| Sample no. | Starting material wetness (%) | Drying Temperature (° C.) | Drying time (Hours) | Wetness During the drying process % | Pressure (mmHg) | Stirring rate (Rounds per minute) |
|---|---|---|---|---|---|---|
| T 1 | 9.5 | 30 | 1 | 5.3 | 60 | Without mixing |
| T 2 | | 30 | 2 | 5.2 | | 4 |
| T 3 | | 45 | 3 | 3 | | |
| T 4 | | 65 | 5 | 0.09 | | |
| T 5 | | 80 | 11 | 0.07 | | |
| T 6 | | 80 | 14 | 0.17 | | |
| T 7 | | 80 | 18 | 0.11 | | |

Example 7

Drying in 200 Grams Scale 200 grams of wet famciclovir were washed with water. The material was dried in a stirred reactor. Form 1 was obtained. The following table describes the drying process and its conditions.

| Sample no. | Starting material wetness (%) | Drying Temperature (° C.) | Drying time (Hours) | Wetness During the drying process % | Pressure (mmHg) | Stirring rate (Rounds per minute) |
|---|---|---|---|---|---|---|
| R 1 | 9.5 | 30 | 1 | 4.8 | 60 | 25 |
| R 2 | | 45 | 2 | 0.1 | | |
| R 3 | | 65 | 3 | 0.12 | | |
| R 4 | | 65 | 5 | 0.06 | | |

Example 8

Drying in 200 Grams Scale 200 grams of wet famciclovir were washed with water. The material was dried in a stirred reactor. Form 1 was obtained. The following table describes the drying process and its conditions.

| Sample no. | Starting material wetness (%) | Drying Temperature (° C.) | Drying time (Hours) | Wetness During the drying process % | Pressure (mmHg) | Stirring rate (Rounds per minute) |
|---|---|---|---|---|---|---|
| D 1 | 9.5 | 45 | 1 | 6.4 | 26 | Without mixing |
| D 2 | | 45 | 2 | 5.6 | | 4 |
| D 3 | | 45 | 4 | 3.4 | | |
| D 4 | | 45 | 5 | 2.17 | | |
| D 5 | | 65 | 7 | 0.6 | | |
| D 6 | | 65 | 9 | 0.3 | | |
| D 7 | | 65 | 12 | 0.2 | | |
| D 8 | | 65 | 15.5 | 0.05 | | |

Example 9

Drying Famciclovir Which Contain more than 40% Wetness 10 grams of famciclovir wet (43% wetness) was dried 10 hours at 30° C., 8 hours at 45° C. and 4 hours at 65° C. There was no melting during the drying process.

Example 10

Process for Preparing Famciclovir in a Large Scale

Into a jacketed reactor equipped with a mechanical stirrer and a reflux condenser, under an inert atmosphere (nitrogen), wet 10% Pd/C (16.7 Kg, 52% $H_2O$), EtAc (376 L) and Cl-Ap (80 Kg) were added. The reaction mixture was heated to 60-70° C. Ammonium formate (17 Kg) was added in 11 portions. The portions were added every 20 min. After 4 hours, all the Cl-Ap was consumed. The reaction mixture was diluted to 64 L and filtered at 40° C.-50° C. A charcoal (4 Kg) was added to the filtrate and the mixture was stirred for 30 min. then the charcoal was filtered out and washed (80 L) EtAc. The wash was added to the filtrate. The filtrate was distillated back to 376 L of EtAc. Precipitation occurred during the distillation. The mixture was heated until a clear solution obtained. Then the solution was cooled to −8 deg for 6 hr. precipitation occurred during the cooling process. After one hr of stirring, the material was filtered out and was washed with water. 50 Kg of wet famciclovir were obtained (66% yield).

The invention has been described in reference to its preferred embodiments. One skilled in the art may appreciate changes that could be made in the preferred embodiments which do not depart from the spirit and scope of the invention.

The invention claimed is:

1. A process for preparing crystalline famciclovir, comprising:
   a) providing a wet crystalline form of famciclovir containing from about 15% to about 40% (wt/wt) solvent;
   b) drying the wet crystalline form of famciclovir of step a) at a temperature of from about 30° C. to about 50° C. to obtain a wet crystalline form of famciclovir; and
   c) drying the wet crystalline form obtained from step b) at a temperature higher than 50° C. to obtain a crystalline form of famciclovir containing less than 1% (wt/wt) solvent;
   wherein the wet crystalline form of famciclovir obtained in step b) contains less than 15% (wt/wt) solvent.

2. The process of claim 1, wherein the wet crystalline form of famciclovir of step a) contains about 15%-40% (wt/wt) solvent and wherein the wet crystalline form of famciclovir obtained in step b) contains less than 15% (wt/wt) solvent.

3. The process of claim 1, wherein the solvent is selected from the group consisting of water, $C_1$-$C_4$ alcohols, $C_5$-$C_8$ alkanes, diisopropyl ether, acetic acid, acetone, 1-butanol, 2-butanol, butyl acetate, tert-buthylmethyl ether, dimethyl sulfoxide, ethanol, ethyl acetate, ethyl ether, ethyl formate, formic acid, heptane, isobutyl acetate, isopropyl acetate, methyl acetate, 3-methyl-1-butanol, methylethyl ketone, methylisobutylketone, 2-methyl-1-propanol, pentane, 1-pentanol, 1-propanol, 2-propanol, and propyl acetate and mixtures thereof.

4. The process of claim 1, wherein the drying in step b) is performed at a temperature of from about 40° C. to about 50° C.

5. The process of claim 4, wherein the drying in step b) is performed at a temperature of about 45° C.

6. The process of claim 1, wherein the temperature of step c) ranges from about 50° C. to about 80° C.

7. The process of claim 1, wherein the temperature of step c) ranges from about 50° C. to about 65° C.

8. The process of claim 1, further comprising drying the crystalline form of famciclovir obtained in step c) at a temperature ranging from about 50° C. to about 80° C. to obtain a crystalline form of famciclovir containing less than 0.5% (wt/wt) solvent.

9. The process of claim 1, further comprising drying the crystalline form of famciclovir obtained in step c) at a temperature ranging from about 50° C. to about 80° C. to obtain a crystalline form of famciclovir containing less than 0.05% (wt/wt) solvent.

10. The process of claim 2, wherein the solvent is water.

11. The process of one of claims 1 and 10, wherein the crystalline form of famciclovir obtained in step c) is famciclovir Form I; wherein Form I is characterized by XRD peaks at 15.5 and 15.9 degree±0.2 degree 2θ.

12. The process of claim 10, wherein the crystalline form of famciclovir obtained in step c) is famciclovir Form I containing less than 10% (wt/wt) of another crystalline form of famciclovir; wherein Form I is characterized by XRD peaks at 15.5 and 15.9 degree±0.2 degree θ.

13. The process of claim 11, wherein the famciclovir Form I contains less than 10% (wt/wt) of crystalline form II of famciclovir; wherein Form II is characterized by XRD peaks at 16.2 and 16.4 degree±0.2 degree 2θ.

14. The process of claim 12, wherein the famciclovir Form I contains less than 2% (wt/wt) of another crystalline form of famciclovir.

15. The process of claim 14, wherein the famciclovir Form I contains less than 2% (wt/wt) of crystalline Form II of famciclovir.

16. The process of claim 1, further comprising washing the wet crystalline form of famciclovir containing about 40% (wt/wt) or less solvent with a wash solvent prior to step a).

17. The process of claim 16, wherein the wash solvent is selected from the group consisting of water, $C_1$-$C_4$ alcohols, $C_5$-$C_8$ alkanes, diisopropyl ether, acetic acid, acetone, 1-butanol, 2-butanol, butyl acetate, tert-buthylmethyl ether, dimethyl sulfoxide, ethanol, ethyl acetate, ethyl ether, ethyl formate, formic acid, heptane, isobutyl acetate, isopropyl acetate, methyl acetate, 3-methyl-1-butanol, methylethyl ketone, methylisobutylketone, 2-methyl-1-propanol, pentane, 1-pentanol, 1-propanol, 2-propanol, and propyl acetate and mixtures thereof.

18. The process of claim 17, wherein the wash solvent is water.

19. The process of claim 16, wherein the wet crystalline form of famciclovir obtained after washing the wet crystalline form of famciclovir containing about 40% (wt/wt) or less solvent prior to step a) contains more than 40% (wt/wt) solvent.

20. The process of one of claims 1 and 19, further comprising drying a wet crystalline form of famciclovir containing more than 40% (wt/wt) solvent at a temperature of from about 25° C. to about 35° C. to obtain the wet crystalline form of famciclovir containing 40% (wt/wt) or less solvent of step a).

21. The process of claim 1, comprising:
a) providing a wet crystalline form of famciclovir containing 40% (wt/wt) or less water;
b) drying the wet crystalline form of famciclovir of step a) at a temperature of from about 30° C. to about 50° C. to obtain a wet crystalline form of famciclovir containing less than about 15% (wt/wt) water; and
c) drying the wet crystalline form obtained in step b) at a temperature higher than 50° C. to obtain a crystalline form I of famciclovir containing less than 1% (wt/wt) water.

22. The process of claim 1, comprising:
a) providing a wet crystalline form of famciclovir containing 40% (wt/wt) or less solvent by drying a wet crystalline form of famciclovir containing more than 40% (wt/wt) solvent at a temperature of from about 25° C. to about 35° C. to obtain the wet crystalline form of famciclovir containing 40% (wt/wt) or less solvent;
b) drying the wet crystalline form of famciclovir obtained in step a) at a temperature of from about 30° C. to about 50° C. to obtain a wet crystalline form of famciclovir containing less than 15% (wt/wt) solvent; and
c) drying the wet crystalline form of famciclovir obtained in step b) at a temperature higher than 50° C. to obtain the crystalline form of famciclovir containing less than 1% (wt/wt) solvent.

23. The process of claim 22, wherein the solvent is water and the crystalline form of famciclovir obtained in step c) is famciclovir Form I containing less than 1% (wt/wt) water.

* * * * *